(12) United States Patent
Chen

(10) Patent No.: US 6,827,910 B2
(45) Date of Patent: Dec. 7, 2004

(54) ELECTRIC OZONE TOOTHBRUSH

(76) Inventor: Ching-Fu Chen, 4F, No. 742, Chmg Ping Rd, Chung Ho City, Taipei Hsien (TW)

(*) Notice: Subject to any disclaimer, the term of this patent is extended or adjusted under 35 U.S.C. 154(b) by 247 days.

(21) Appl. No.: 10/128,464

(22) Filed: Apr. 22, 2002

(65) Prior Publication Data

US 2003/0198580 A1 Oct. 23, 2003

(51) Int. Cl.$^7$ .............................. B01J 19/08; A46B 9/04
(52) U.S. Cl. ............................ 422/186.07; 422/186.12; 15/167.1
(58) Field of Search ..................... 422/186.07, 186.12; 15/167.1

(56) References Cited

U.S. PATENT DOCUMENTS 4,743,199 A * 5/1988 Weber et al. ............... 433/216
5,727,273 A * 3/1998 Pai .............................. 15/22.1

* cited by examiner

Primary Examiner—Steven Versteeg
(74) Attorney, Agent, or Firm—Pro-Techtor International Services

(57) ABSTRACT

An electric ozone toothbrush mainly has a guide tube installed in an interior portion of a handle and a brush head of a regular electric toothbrush connecting with a bristle end of the brush head; the other end of the guide tube joins with a coil tube of an ozone generator; an air pump disposed inside the ozone generator guides the ozone into the bristle end of the brush head such that the released ozone sterilizes, deodorizes, whitens the teeth, disinfects and detoxifies during the brushing application of the electric toothbrush.

3 Claims, 4 Drawing Sheets

ELECTRIC OZONE TOOTHBRUSH

BACKGROUND OF THE INVENTION

1) Field of the Invention

The present invention relates to an electric ozone toothbrush, more particularly to an electric toothbrush capable of synchronously utilizing the ozone released from an ozone generator to sterilize, deodorize, whiten the teeth, disinfect, ease pain and decontaminate during tooth brushing.

2) Description of the Prior Art

Accordingly, although a conventional electric toothbrush is capable of cleansing the teeth and massage the gum, it is unable to sterilize, deodorize whiten the teeth or disinfect; more or less, every one has some tooth problems; therefore to have a good hygienic habit is more important than seeking dentist's help when problems occur.

In view of the abovementioned, the inventor of the present invention guides the ozone into an electric toothbrush through utilizing the powerful strength of the ozone molecule as the strong oxidizing agent to radically sterilize the bacteria and virus existing among the teeth and completely oxidize and decompose the cancer causing chlorine in the faucet water thereby benefiting the general public.

SUMMARY OF THE INVENTION

Therefore, the primary objective of the present invention is to provide an electronic toothbrush which engages a coil tube of an ozone generator to a guide tube inside an electronic toothbrush thereby utilizing an air pump inside an ozone generator to guide the ozone into a bristle end of a brush head of the toothbrush for synchronously achieving the effects of sterilization, deodorization, whitening the teeth, disinfecting and detoxification during tooth brushing.

Another objective of the present invention is to provide an electronic toothbrush wherein, while not engaging with an electronic toothbrush, the coil tube of the ozone generator works independently as an air cleanser to utilize the colorless and unique gas with fresh grass flavor discharged by the ozone generator as a deodorizing agent for cleansing lavatories.

Yet another objective of the present invention is to provide an electronic toothbrush wherein, while not engaging with an electronic toothbrush, the coil tube of the ozone generator engages with a bubble body placed in the water for utilizing the discharged ozone to completely oxidize and decompose the cancer causing chlorine, saturate and oxidize the water, reduce the size of the water molecule such that it can be fast absorbed in a human body thereby increasing the blood content and strengthening metabolism; therefore, to wash the face or take a shower with the ozone water is capable of achieving the effects of sterilization, skin whitening, and decontamination for beautifying, oxygenating and vitalizing the skin.

To enable a further understanding of the structural features and the technical contents of the present invention, the brief description of the drawings below is followed by the detailed description of the preferred embodiment.

DETAILED DESCRIPTION OF THE PREFERRED EMBODIMENTS

Figure 1:
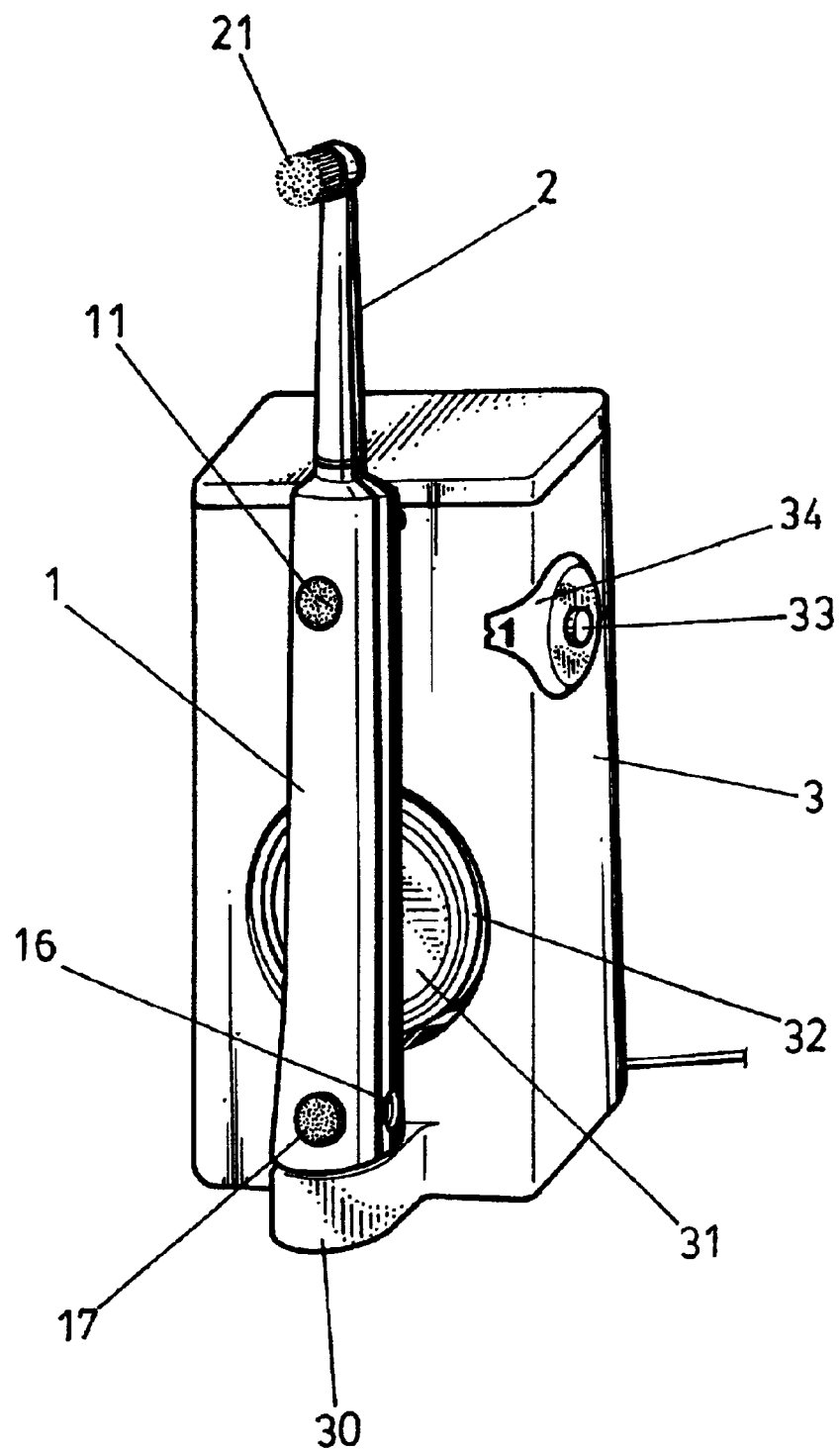
FIG. 1 is an external view of the present invention.
Figure 2:
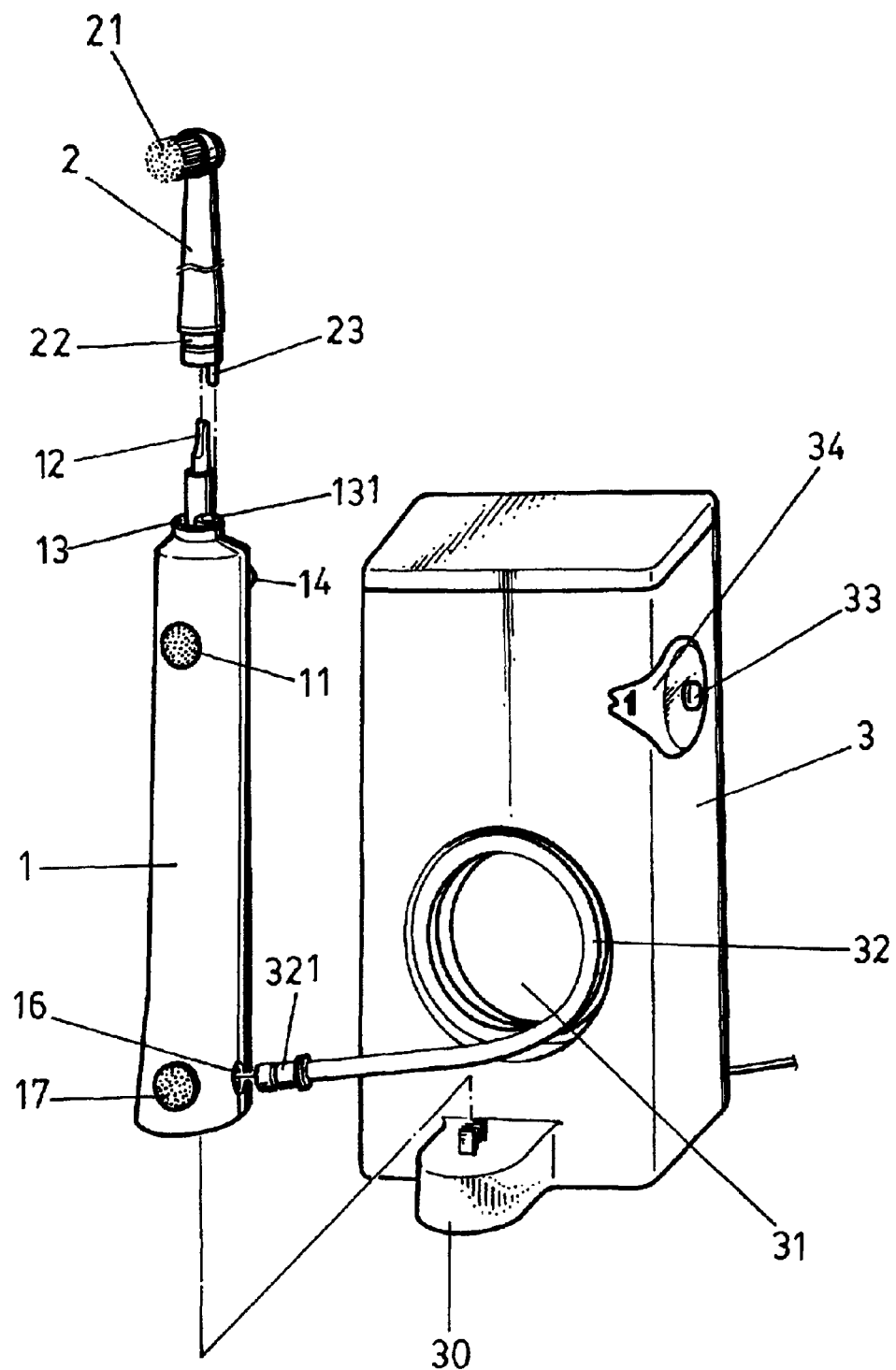
FIG. 2 is a partially enlarged drawing of the present invention.

Referring to all of the indicated figures, the present invention of an electric ozone toothbrush comprises a handle (1), a brush head (2) and an ozone generator, wherein the electric toothbrush thereof is similar to that of a conventional electric toothbrush; the handle (1) has a press button (11) thereon and a transmission shaft (12) is disposed at a top end thereof; at a normal time, the electric toothbrush is placed on an induction charger (30) for charging the electric toothbrush at a proper time; the top end of the brush head (2) is a bristle (21) and a fast joint (22) at the bottom end extends into a tube hole (13) of the handle (1); a press button (14) on the back side of the handle (1) controls the clamping of the brush head (2); the ozone generator (3) is a conventional product with an integrated-circuit control panel and an air pump; they are not included as the patented features of the present invention, therefore they are not indicated in the Figures.

Figure 3:
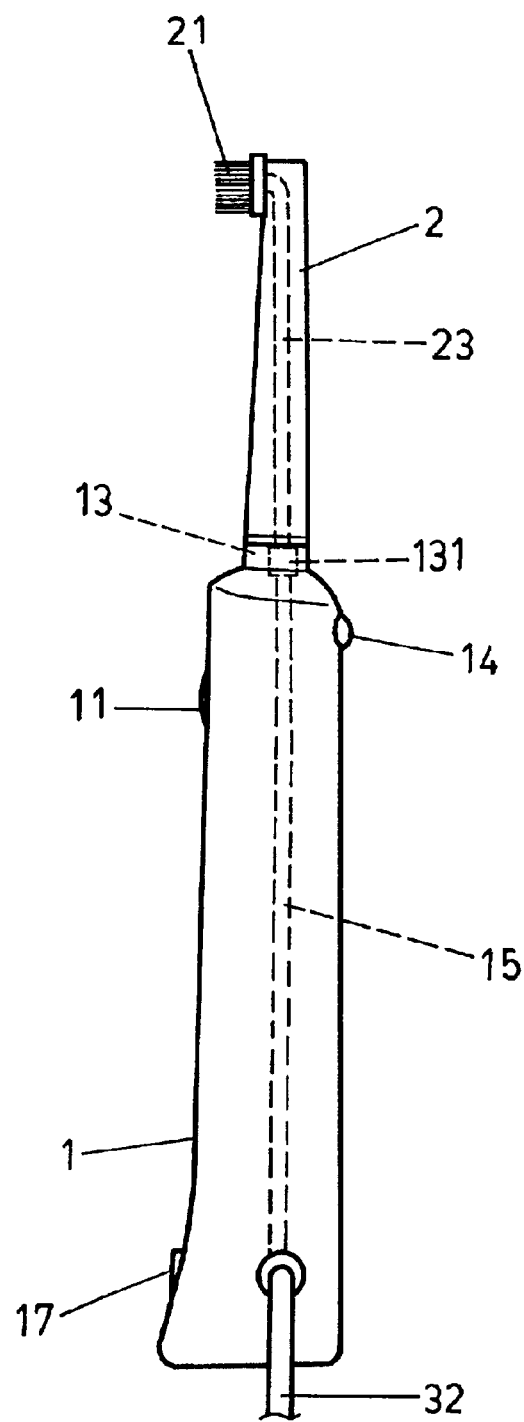
FIG. 3 is a cross-sectional and schematic drawing of the present invention of an electric ozone toothbrush.

Referring to FIG. 3, the interior portion of the handle (1) is disposed with a guide tube (15) with its top end inserted into a sleeve tube (131) of a tube hole (13) for positioning; a tube channel (31) at the front rim of the ozone generator (3) is disposed with a coil tube (32) therein; the interior portion of the coil tube (32) engages with an outlet of the ozone generator (3); a fast joint (321) of the other end of the coil tube (32) extends in to an insert hole (16) at the bottom end of the handle (1); a control button (17) is disposed on the handle (1) located on the lateral side of the insert hole (16) for facilitating the clamping of the coil tube (32). The air pump guides the ozone from the ozone generator (3) into the coil tube (32) and then into the guide tube (15) of the handle (1). Furthermore, a guide tube (23) is also disposed inside the brush head (2), as indicated in FIG. 3. The top end of the guide tube (23) engages with the end of the bristle (21) while the bottom end extends outside the brush head (2) portion and inserts into the sleeve tube (131) on the lateral side of the tube hole at the top end of the handle (1) for forming a communicating path with the guide tube (15) inside the handle (1). One end of the ozone generator (3) has an ozone power button (33) and an ozone density adjusting button (34) for adjusting the density of the discharged ozone.

When not engaging with the electric toothbrush, the coil tube (32) of the ozone generator (3) utilizes the discharged ozone as an air cleanser by using the discharged colorless gas with unique fresh grass flavor as a deodorizing agent for cleansing lavatories.

Figure 4:
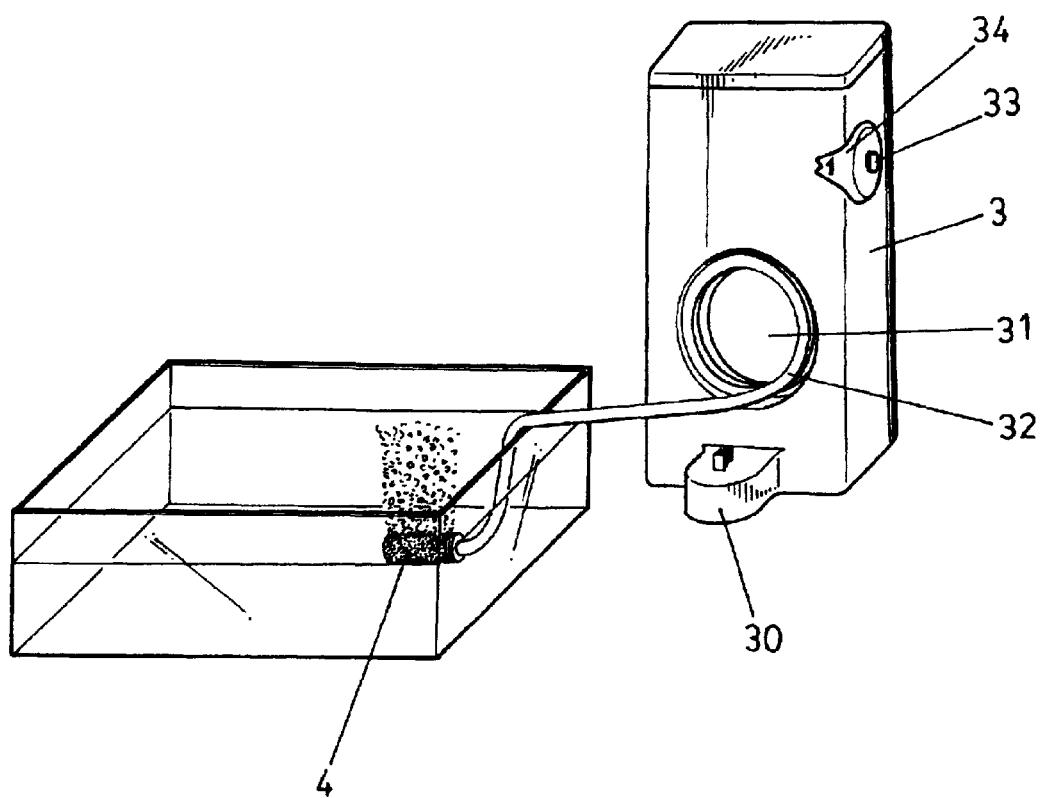
FIG. 4 is a drawing of an exemplary embodiment of the present invention.

Referring to FIG. 4, when not engaging with the electric toothbrush, the coil tube (32) of the ozone generator (3) engages a bubbled body (4) or an air stone placed inside the water; the ozone completely oxidizes and decomposes the cancer causing chlorine in the faucet water for saturating and oxidizing the water, as well as reducing the water molecule to be absorbed easily by the human body, increasing the blood content and strengthening metabolism; therefore, to wash the face or take a shower with the ozone water is capable of achieving the effects of beautifying, oxygenating and vitalizing the skin through sterilization, whitening and decontamination.

In summation of the abovementioned, the present invention of an electric ozone toothbrush is a structure formed by improving a conventional electric toothbrush and utilizing the ozone generated from the ozone generator to achieve the effects of sterilization, deodorization, tooth whitening, disinfection and decontamination.

It is of course to be understood that the embodiment described herein is merely illustrative of the principles of the invention and that a wide variety of modifications thereto may be effected by persons skilled in the art without departing from the spirit and scope of the invention as set forth in the following claims.

What is claimed is:

1. An electric ozone toothbrush comprising:

a handle, a brush head and an ozone generator; wherein a power button is disposed on the handle, a quick connect joint at a bottom end of the brush head extends into a tube hole of the handle, a guide tube is disposed inside the handle, a coil tube is disposed inside a slot of the ozone generator, with an interior portion of the coil tube engaging the ozone generator, an end of the coil tube extends into the handle to engage the guide tube, a top end of the guide tube engages with a head guide tube inside the brush head and extends to a bristle end of the brush head, ozone generated from the ozone generator is guided into the guide tubes of the handle and the brush head to enter the bristle end via the coil tube; and wherein when the coil tube of the ozone generator is not engaging the guide tube of the handle, the coil tube of the ozone generator engages with a bubble body placed in a vessel of water.

2. An electric ozone toothbrush according to claim 1, wherein:

one end of the coil tube of the ozone generator is disposed with a quick connect joint and an insert hole is disposed on the handle for the insertion of the quick connect joint to facilitate engagement of the coil tube and the handle.

3. An electric ozone toothbrush according to claim 1, wherein:

the guide tube inside the handle inserts into a sleeve tube of a tube hole at the top end for positioning while the guide tube inside the brush head also inserts into the sleeve tube of the tube hole of the handle.

* * * * *